(12) United States Patent
Mallia

(10) Patent No.: US 6,540,897 B1
(45) Date of Patent: Apr. 1, 2003

(54) DIRECT DETECTION OF HISTIDINE TAGGED BIOMOLECULES ON ELECTROPHORETIC GEL

(75) Inventor: A. Krishna Mallia, Rockford, IL (US)

(73) Assignee: Pierce Chemical Company, Rockford, IL (US)

( * ) Notice: Subject to any disclaimer, the term of this patent is extended or adjusted under 35 U.S.C. 154(b) by 162 days.

(21) Appl. No.: 09/615,897

(22) Filed: Jul. 13, 2000

(51) Int. Cl.[7] .............................................. G01N 27/447
(52) U.S. Cl. ....................... 204/461; 204/462; 204/612; 204/613
(58) Field of Search ................................. 204/456, 461, 204/462, 606, 612, 613

(56) References Cited

U.S. PATENT DOCUMENTS 5,792,330 A * 8/1998 Petersen et al. ............ 204/451

FOREIGN PATENT DOCUMENTS

WO WO 98/15293 * 4/1998

OTHER PUBLICATIONS

Chan et al, Analytical Chemistry, 65, pp. 158–163, 1993.*
Lamture et al, Tetrahedron Letters, 34, pp. 4141–4144, 1993.*
Lamture et al, Bioconjugate Chemistry, 6, pp. 88–92, 1995.*

* cited by examiner

*Primary Examiner*—Robert J. Warden, Sr.
*Assistant Examiner*—Kaj K. Olsen

(57) ABSTRACT

A method is disclosed for the detection of a His-tagged target biomolecule while said molecule remains in the gel in which it has been separated from other constituents by electrophoresis. The method involves, while the separated His-tagged biomolecule remains in the gel, forming a chelate between the His-tagged molecule, a lanthanide metal ion which exhibits fluorescence, and a sensitizer which enhances the fluorescence of the ion. The gel is then exposed to a u.v. light source to thereby generate a fluorogenic signal indicating the presence of the chelate and, in turn, the His-tagged biomolecule. The fluorogenic signal can then be detected either by direct visualization and/or by other means, such as photographically, e.g., film or charged coupled device (CCD) imaging.

8 Claims, No Drawings

US 6,540,897 B1

DIRECT DETECTION OF HISTIDINE TAGGED BIOMOLECULES ON ELECTROPHORETIC GEL

FIELD OF INVENTION

The present invention relates to the fluorometric detection of target substances and, more particularly, to detection of histidine tagged biomolecules directly on the gel in which they have been separated by electrophoresis.

BACKGROUND OF INVENTION

Capture of target substances such as biomolecules on solid phases has been used for years in order to facilitate their subsequent identification. One method of capture is generally designated as "blotting" whereby the target substance is applied, directly or by transfer, from another media, to a membrane such as nitrocellulose, polyvinyllidene difluoride (PVDF), or nylon.

Blotting is most frequently used in combination with known gel electrophoresis procedures (single or two-dimensional) whereby the target substance is first electrophoretically separated on a gel from other substances. It is then transferred to a membrane for specific detection of the target and its location on the membrane.

Procedures for electrophoretic separation with subsequent blotting onto a membrane are generally referred to in the literature as either Western blotting, Northern blotting or Southern blotting. Western blotting refers to the identification of proteins as target substances, while the latter two procedures refer to identification of target RNA and DNA sequences, respectively.

An application in which Western blotting has been utilized is with respect to recombinantly produced proteins which have been tagged with a substance to facilitate detection and purification. A popular tag is the "His-tag" which is a series, generally about 3–10 and preferably about 36, of histidine residues. Advantages associated with the use of the His-tag include minimal addition of amino acid groups to the recombinant protein, that the tag is poorly immunogenic, and that it usually does not interfere with protein folding.

Histidine is known to chelate with a number of metals, see "Immobilized Affinity Ligand Techniques," (1992) Hermanson, Mallia, and Smith, Academic Press, 1992. Accordingly, Western blot detection of a histadine tagged protein, i.e., subsequent to electrophoretic separation on a gel of proteins in the lysate and blotting from the gel onto a membrane, using detectable nickel conjugate systems such nickel chelated to horseradish peroxidase or nickel-nitriloacetic acid conjugates are in current use.

A drawback, however, associated with Western and other blotting techniques is that they require time consuming and cumbersome steps. These include transferring the target substance from the electrophoretic gel to the membrane on which the substance is to be detected and blocking and washing the membrane. It is with respect to eliminating these procedures that the present invention is directed.

SUMMARY OF THE INVENTION

Therefore, in accordance with one aspect of the present invention, there is provided a method for the detection of a His-tagged target biomolecule while said molecule remains in the gel in which it has been separated from other constituents by electrophoresis. The process of this invention involves separating a His-tagged biomolecule from other substances by electrophoresis over a gel and, while the separated His-tagged biomolecule remains in the gel, forming a chelate between the His-tagged molecule, a lanthanide metal ion which exhibits fluorescence, and a sensitizer which enhances the fluorescence of the ion. The gel is then exposed to a u.v. light source to thereby generate a fluorogenic signal indicating the presence of the chelate and, in turn, the His-tagged biomolecule. The fluorogenic signal is then detected either by direct visualization and/or by other means, such as photographically, e.g., film or charged coupled device (CCD) imaging.

In accordance with a further aspect of the present invention, there is provided a kit for the direct detection of histidine tagged biomolecules on an electrophoretic gel. The kit contains, as essential items, two separately packaged components and written instructions for use of the components in the direct detection of a His-tagged biomolecule on electryphoretic gel. One of the packaged components is an aqueous solution of a lanthanide metal ion which exhibits fluorescence. The other component is an aqueous solution of a sensitizer which enhances the fluorescence of the lanthanide metal ion.

DESCRIPTION OF THE INVENTION

U.S. Pat. No. 5,637,509 identifies Dy(+3), Sm (+3), Tb(+3) and Eu(+3) as lanthanide metal ions which exhibit fluorescence and, accordingly, are useful. Of these, terbium and europium metal ions (Tb(+3) and Eu (+3) ) are most useful herein with terbium being particularly preferred since especially large increases in fluorescence can be achieved. Barela and Sherry, (1976) Analytical Biochemistry, 71, 351–357. In practicing the invention, the metals can be applied directly to the gels containing the separated His-Tag substances as aqueous solutions of their water soluble salts, e.g., as chlorides. As long as sufficient metal ion is present to chelate with available histidine residues, the concentration of the metal ion in solution is not critical. About 0.1 mM solutions are useful for most applications.

A number of compounds have been identified over the years as sensitizers which, when chelated with a lanthanide metal ion, enhance the fluorescence of the lanthanide metal ion and are considered to be useful herein. Examples of such compounds can be found in the following: U.S. Pat. Nos. 5,656,433 and 5,859,215 and WO8707955 and EP0288256.

Of the many known sensitizers, dipicolinic acid (pyridine, 2,6 dicarboxylic acid) and derivatives thereof are particularly useful herein in enhancing the fluorescent signal of lanthanide metal ions. Barela, supra, Lamture and Wensel (1993) Tetrahedron Letters, Vol. 34, No. 26 pp. 4141, Lamture and Wensel, (1995) Bioconjugate CHEM,6, 88–92 (1995). For use in the present invention, the acid itself is preferred since no practical advantages are realized with the use of other dipicolinic acids, i.e., derivatives thereof; the important aspect being the presence of the carboxylic acids at the 2 and 6 positions of the pyridine ring.

As with the lanthanide metal, the sensitizer employed can be applied to the gel as an aqueous solution, generally appropriately buffered to a pH of about 7 using, e.g., a TRIS (tris (hydroxymethyl) aminomethane) buffer. Similarly concentration is not critical so long as sufficient acid is present to chelate with the lanthanide metal present so as to enhance fluorescence. About a 2 mM concentration is useful.

The present invention is applicable to the detection of His-tagged target biomolecules which have been separated from other constituents by means of gel electrophoresis. It finds most general application currently with respect to the detection of His-tagged proteins which have been recombinantly expressed and then electrophoretically separated from other host cell constituents in the crude lysate. It may also find utility in the direct detection of oligonucleotides currently detected by Northern or Southern blot techniques. Concerning gel electrophoresis techniques, the procedure commonly known as SDS-PAGE, (using sodium dodecyl sulfate in polyacrylamide gels), is useful for the separation of the His-tagged proteins when, as most commonly practiced, separation by molecular mass is desired. For tagged oligonucleotides, electrophoresis in agarose is generally employed.

In one manner of carrying out the present invention, after electrophoresis of a crude lysate containing a His-tagged biomolecule, the gel is washed with water and then incubated in a solution of the lanthanide metal ion to effect chelate formation with the His-tagged biomolecule, followed again by washing to remove excess metal ion, thereby reducing background. Then the gel is incubated in a buffered solution of the sensitizer to chelate the sensitizer to the ion chelated to the His-tagged molecule. After removal from the latter solution and washing, the gel is irradiated with ultraviolet light (300 nm) using, for example, a transluminator illumination box. The His-tagged substance can be observed as a luminescent band on the gel. The gel can then be stained in a conventional manner (with e.g., coomassie stain) for a total protein profile determination.

The following Example illustrates the present invention:

EXAMPLE 1

*E. coli* M15 cells were transformed with constructs expressing 6×His-tagged rat urate oxidase (UOX, 35 kDa), baculovirus polyhedrin (PHD, 30 kDa) and mouse dihydrofolate reductase (DHFR, 22 kDa), respectively. The transformed cells were grown at 37° C. in LB media, and induced with 0.2 mM IPTG for 2 hours. After induction, the cells were harvested, lysed with 1×SDS-PAGE sample buffer, and loaded onto a 4–20% gradient precasted SDS-PAGE gel and subjected to electrophoresis.

After electrophoresis, the gel was first washed with 100 ml of D.I. water for 20 minutes to remove SDS. Next, the gel was transferred into 50 ml of a solution of 0.1 mM terbium chloride in water and agitated gently for 5 minutes. The gel was then washed with 100 ml of D.I water with gentle agitation for 15 minutes, and this wash step was repeated once.

The gel was then transferred into 50 ml of a solution of 2 mM dipicolinic acid in a buffer (25 mM Tris and 150 mM NaCl, pH 7.2) and gently agitated for 15 minutes followed by two 15 minute washings with DI water.

The gel was then placed on top of a Transluminator box and irradiated with ultraviolet light (300 nm). The His-tagged UOX protein was seen as a luminescent band on the polyacrylamide gel, the other two proteins exhibiting no visible bands.

After 6×His-tagged protein visualization as described above, the gel was placed in 50 ml of coomassie staining reagent (GelCode® Blue Stain Reagent from Pierce Chemical Company) for 1 hour and then washed with D.I. water. The blue bands for all three proteins were clearly visible.

As illustrated in the example, the time required for detection of 6×His-tagged recombinant protein by means of the present invention is less than two hours since it does not require membrane transfer, blocking, and blotting steps. These latter steps, employed in Western blotting, can take up to 6–8 hours.

Moreover, membrane-based detection methods require the transfer of substances from the gel to the membrane, a process which is not always 100% efficient. Direct detection, as illustrated herein, provides consistent results by eliminating variable factors associated with the membrane based methods.

Furthermore, yielding a fluorescent stain, the method of the present invention does not interfere with other colorimetric stains, such as coomassie. Thus, the same gel can be used for both 6×His-tag detection and total protein detection. This feature provides the ability to estimate the expression level of a recombinant protein on the same gel after determining whether the recombinant protein is 6×His-tagged.

The subject matter of the patents and articles identified in this specification is incorporated herein by reference.

What is claimed is:

1. A method for the direct detection of a histidine tagged biomolecule on an electrophoretic gel comprising (1) separating the biomolecule from other substances by electrophoresis on a gel, (2) while said biomolecule remains so separated, forming a chelate between said biomolecule, a lanthanide metal ion which exhibits fluorescence, and a sensitizer which enhances the fluorescence of the ion, and (3) exposing the gel containing said chelate to a u.v. light source thereby generating a fluorescent signal indicative of the presence of the chelate and, in turn, the histidine tagged biomolecule, and (3) detecting the signal so generated.

2. The method of claim 1 wherein the lanthanide metal ion is terbium or europium and the sensitizer is a dipicolinic acid.

3. The method of claim 2 wherein the lanthanide metal ion is terbium.

4. The method of claim 2 or 3 wherein the dipicolinic acid is pyridine, 2,6 dicarboylic acid.

5. The method of claim 1 wherein said chelate of the histidine tagged biomolecule, the lanthanide metal ion and the dipicolinic acid is formed by first chelating the histidine tagged biomolecule with the lanthanide metal ion followed by chelation with the sensitizer.

6. The method of claim 5 wherein the lanthanide metal ion is terbium or europium and the sensitizer is a dipicolinic acid.

7. The method of claim 6 wherein the lanthanide metal ion is terbium.

8. The method of claim 6 or 7 wherein the dipicolinic acid is pyridine, 2,6 dicarboylic acid.

* * * * *